(12) United States Patent
Gardi et al.

(10) Patent No.: US 9,070,190 B2
(45) Date of Patent: Jun. 30, 2015

(54) ULTRASOUND IMAGING SYSTEM AND METHODS OF IMAGING USING THE SAME

(75) Inventors: Lori Anne Gardi, London (CA); Donal B. Downey, Kamloops (CA); Aaron Fenster, London (GB)

(73) Assignee: Robarts Research Institute, London Ontario (CA)

( * ) Notice: Subject to any disclaimer, the term of this patent is extended or adjusted under 35 U.S.C. 154(b) by 768 days.

(21) Appl. No.: 13/233,449

(22) Filed: Sep. 15, 2011

(65) Prior Publication Data

US 2012/0004539 A1    Jan. 5, 2012

Related U.S. Application Data

(60) Division of application No. 12/706,476, filed on Feb. 16, 2010, now abandoned, which is a continuation of application No. 10/585,984, filed as application No. PCT/CA2005/000032 on Jan. 12, 2005, now abandoned.

(60) Provisional application No. 60/535,825, filed on Jan. 13, 2004.

(51) Int. Cl.
*A61N 5/00* (2006.01)
*G06T 7/00* (2006.01)
*A61B 8/08* (2006.01)
*G06T 7/20* (2006.01)
*A61B 10/02* (2006.01)
*A61B 19/00* (2006.01)

(52) U.S. Cl.
CPC .............. *G06T 7/004* (2013.01); *A61B 8/0833* (2013.01); *A61B 10/0233* (2013.01); *A61B 19/2203* (2013.01); *A61B 2019/5276* (2013.01); *A61B 2019/5289* (2013.01); *G06T 7/2053* (2013.01); *G06T 2207/30004* (2013.01); *A61B 8/483* (2013.01)

(58) Field of Classification Search
CPC ................ A61B 17/3403; A61B 2019/507; A61B 8/0841; A61B 2019/5289; G06T 2207/30004
See application file for complete search history.

(56) References Cited

U.S. PATENT DOCUMENTS

| 6,310,477 B1 | 10/2001 | Schneider |
| 2003/0135119 A1 | 7/2003 | Lee et al. |
| 2003/0225325 A1 | 12/2003 | Kagermeier et al. |

FOREIGN PATENT DOCUMENTS

| CA | 2 403 526 A1 | 10/2001 |
| WO | WO 02/096507 A2 | 12/2002 |

OTHER PUBLICATIONS

Draper et al., "An Algorithm for Automatic Needle Localization in Ultrasound-Guided Breast Biopsies", *Medical Physics*, 27:1971-1979 (2000).

(Continued)

*Primary Examiner* — Elmer Chao
(74) *Attorney, Agent, or Firm* — Tarolli, Sundheim, Covell & Tummino LLP

(57) ABSTRACT

A method of registering the position of an object moving in a target volume in an ultrasound imaging system includes capturing a first ultrasound image of a target volume. A second ultrasound image of the target volume is then captured after the capturing of the first ultrasound image. The position of the object in the target volume is identified using differences detected between the first and second ultrasound images. In another aspect, a region of interest in the target volume is determined. A segment of an operational scan range of a transducer of the ultrasound imaging system encompassing the region of interest is determined. The transducer is focused on the segment of the operational scan range during image capture.

39 Claims, 14 Drawing Sheets

(56) References Cited

OTHER PUBLICATIONS

Fenster et al., "Three-Dimensional Ultrasound imaging", *Phys. Med. Biol.*, 46:R67-R99 (2001).
Moskalik et al., "Registration of Three-Dimensional Compound Ultrasound Scans of the Breast for Refraction and Motion Correction", *Ultrasound in Med.& Biol.*, 21:769-778 (1995).
Wei et al., "Robotic Aided 3D TRUS Guided Intraoperative Prostate Brachytherapy", *Proceedings of the SPIE*, 5367:361-370 (2004).
European Search Report dated Apr. 5, 2011, 6 pgs.

ULTRASOUND IMAGING SYSTEM AND METHODS OF IMAGING USING THE SAME

RELATED APPLICATIONS

This application is a divisional of U.S. patent application Ser. No. 12/706,476, filed Feb. 16, 2010, which is a continuation of U.S. patent application Ser. No. 10/585,984, filed Jul. 18, 2007 which corresponds to PCT International Application No. PCT/CA2005/000032, filed Jan. 12, 2005 and which claims benefit of U.S. Provisional Patent Application Ser. No. 60/535,825, filed Jan. 13, 2004. The subject matter of the aforementioned applications is incorporated herein by reference.

FIELD OF THE INVENTION

The present invention relates generally to imaging systems and, specifically, to an ultrasound imaging system and methods of imaging using the same.

BACKGROUND OF THE INVENTION

Ultrasound-guided interventional procedures such as breast biopsies and prostate brachytherapy are well-known. Needles can be inserted into the body and either obtain a biopsy sample or deliver a dose of a selected therapy. For biopsies, it is desirable to target a specific volume when obtaining a tissue sample. Where a dose is being administered to a target volume, it is desirable to track the precise location of the needle delivering the dose in real-time to ensure that the therapy is delivered according to plan.

Radioactive seeds can be used as a therapy to treat tumors in prostates. In order to ensure adequate coverage of the therapy, it is desirable to implant the seeds a pre-determined distance apart if the distance between the seeds is too large, tissue between the seeds may not receive the amount of therapy needed for the treatment. If, instead, the seeds are too closely positioned, the tissue can be over-exposed. Further, it is desirable to ensure that the implantation of the seeds is limited to the target volume in order to prevent the therapy from adversely affecting otherwise healthy tissue.

In robotic-aided interventional procedures, such as robot-aided and ultrasound-guided prostate brachytherapy as well as free-hand ultrasound-guided biopsy procedures, a needle is inserted free from parallel trajectory constraints. Oblique insertion of the needle, however, can result in the needle intersecting the two-dimensional ("2D") trans-rectal ultrasound ("TRUS") image and appearing as a point, leading to blind guidance.

Some investigators have developed automatic needle segmentation methods to locate needles for biopsies and therapy. These methods, however, require that the needle be completely contained in the 2D ultrasound ("US") image.

The general operation of ultrasound transducers has provided less-than-desirable image resolution in some instances. Image quality for less significant regions distal from the target volume or even along the shaft of the needles may not be as critical as for the region surrounding the needles. This is especially true for therapy where seeds are being implanted in a target volume. Current ultrasound techniques, however, are directed to the capture of generally evenly distributed images, regardless of the content of the volume targeted by the images.

It is, therefore, an object of the present invention to provide a novel method of imaging using an ultrasound imaging system.

SUMMARY OF THE INVENTION

In an aspect of the invention, there is provided a method of registering the position of an object moving in a target volume in an ultrasound imaging system, comprising:
 capturing a first ultrasound image of a target volume;
 capturing a second ultrasound image of said target volume after said capturing of said first ultrasound image; and
 identifying the position of said object in said target volume using differences detected between said first and second ultrasound images.

In a particular aspect, a difference map of the differences between the first and second ultrasound images is generated. The difference map can be thresholded to identify significant changes between the first and second ultrasound images. In another particular aspect, the object is a needle, and the difference map is filtered to identify voxels in the difference map corresponding to a characteristic of the needle. In a further particular aspect, the first ultrasound image is captured prior to entry of the object in the target volume.

In another aspect of the invention, there is provided an ultrasound imaging system for registering the position of an object moving in a target volume, comprising:
 a transducer for capturing a first ultrasound image and a second ultrasound image of a target volume; and
 a processor for detecting differences between said first and second ultrasound images to identify the position of said object in said target volume.

In a particular aspect, the processor generates a difference map from the first and second ultrasound images identifying the differences therebetween. The processor can threshold the difference map to identify significant differences between the first and second ultrasound images.

In a further aspect of the invention, there is provided a method of imaging using an ultrasound imaging system operable to capture image data from a target volume, comprising:
 determining a region of interest in the target volume;
 determining a segment of an operational scan range of a transducer of said ultrasound imaging system encompassing said region of interest; and
 focusing said ultrasound imaging system on said segment of said operational scan range during image capture.

In a particular aspect, the region of interest is an area of expected activity of an object. In another particular aspect, the object is a needle, and the region of interest includes the area along a trajectory of the needle beyond a tip of the needle. In a further particular aspect, the determining of the region of interest includes the expected position of a needle in the target volume. The transducer can be, for example, a rotational transducer. In still other particular aspects, the focusing includes capturing image data in the segment of the operational scan range at a greater scan density than outside of the segment of the operational scan range, or capturing image data only in the segment of the operational scan range.

In a still further aspect of the invention, there is provided an ultrasound imaging system, comprising:
 a transducer for capturing ultrasound images of a target volume; and
 a processor for determining a region of interest in the target volume, for determining a segment of an operational scan range of said transducer encompassing said region of interest, and for directing said transducer to focus on said segment of said operational scan range.

In a particular aspect, the processor determines an area of expected activity to determine the region of interest. In another particular aspect, the transducer is a rotational transducer and the processor determines an angular sector of the operational scan range of the rotational transducer. In a further particular aspect, the processor directs the transducer to capture image data in the segment of the operational scan range at a greater scan density than outside of the segment of the operational scan range. In a still further particular aspect, the processor directs the transducer to capture image data only in the segment of the operational scan range.

The invention enables the position of the needle to be accurately determined. By only analyzing image data that varies significantly between two ultrasound images, the needle can be readily differentiated from complex backgrounds in the ultrasound images. Further, by focusing on a segment of the operational scan range of the transducer of the ultrasound imaging system during image capture, more detailed image data can be captured around the needle to enable its position to be determined with a desired level of accuracy. This can be achieved without sacrificing the scanning speed in some cases.

BRIEF DESCRIPTION OF THE DRAWINGS

Embodiments will now be described, by way of example only, with reference to the attached Figures, wherein.

DETAILED DESCRIPTION OF THE EMBODIMENTS

The method of registering the position of an object such as a needle provides for the near real-time identification, segmentation and tracking of needles. It has a wide range of applications, such as biopsy of the breast and liver and image-guided interventions such as brachytherapy, cryotherapy, as well as other procedures that require a needle or needles to be introduced into soft tissues and be positioned accurately and precisely. The use of the method is described in robot-aided 3D US-guided prostate brachytherapy for the purpose of illustration.

Transperineal prostate brachytherapy provides an improved alternative for minimally-invasive treatment of prostate cancer. Pubic arch interference ("PAI") with the implant path, however, occurs in many patients with large prostates and/or a small pelvis. These patients cannot be treated with current brachytherapy using parallel needle trajectories guided by a fixed template, because the anterior and/or the antero-lateral parts of the prostate are blocked by the pubic bone.

To solve the PAI problems, it is desirable to free needle insertions from parallel trajectory constraints. Oblique trajectories allow patients with PAI to be treated with brachytherapy without first undergoing lengthy hormonal downsizing therapy. In addition, changes in the prostate size prior to implantation, where the therapy is determined in advance of the procedure, and during the implantation, due to swelling of the prostate, may require re-optimization of the dose plan. The combination of precision 3D TRUS imaging, dosimetry and oblique needle insertion trajectories can provide the tools needed for dynamic re-optimization of the dose plan during the seed implantation procedure by allowing dynamic adjustments of the needle position to target potential "cold spots". Cold spots are areas more than a desired distance from seed implantation locations, resulting in less-than-desired exposure. Further, the dosimetry can be dynamically adjusted to compensate for deviations in the actual needle trajectories or shifting in the target volume.

Figure 1:
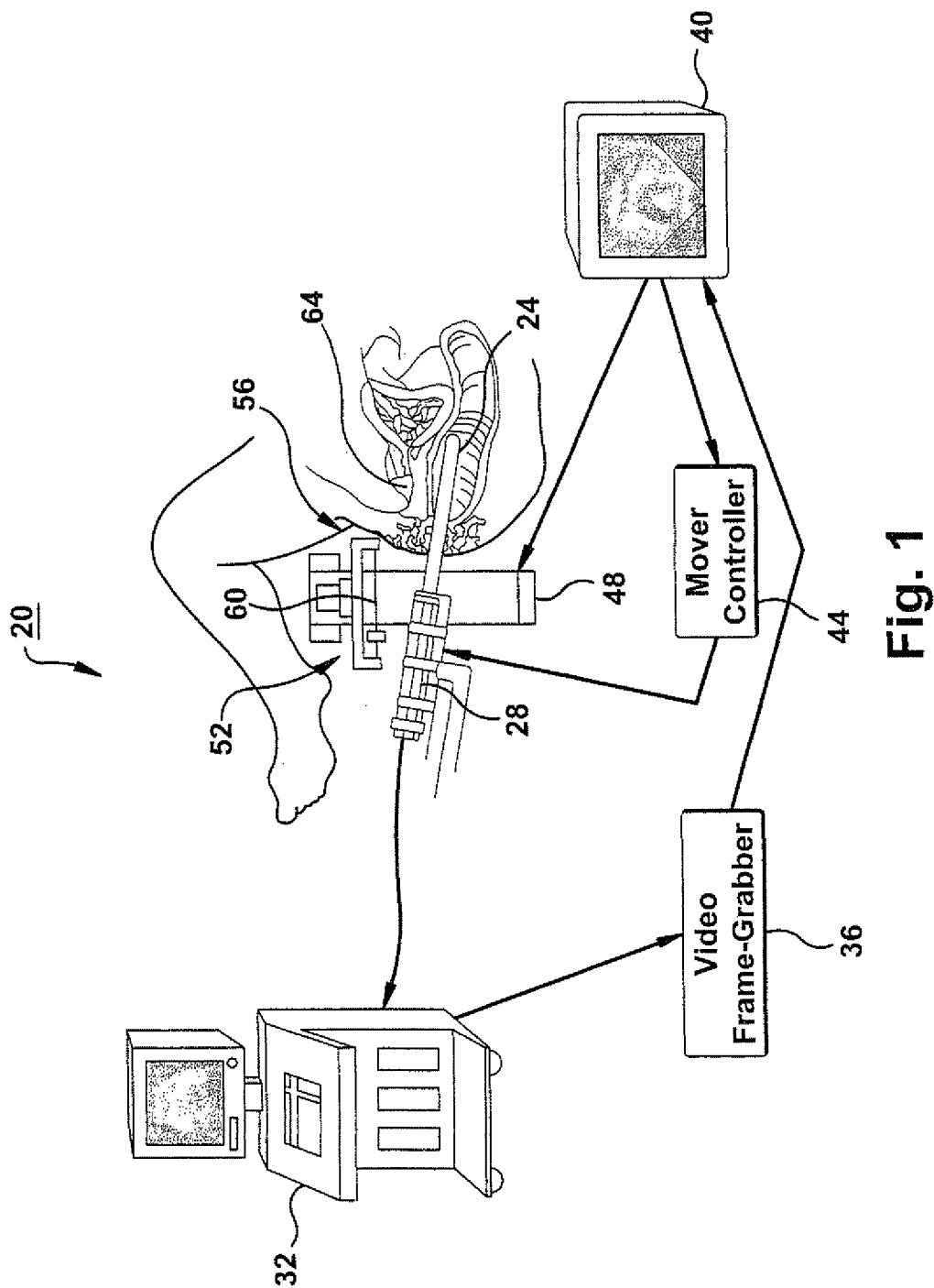
FIG. 1 is a schematic diagram of an ultrasound imaging system for imaging a target volume in a subject.

A 3D TRUS-guided robot-aided prostate brachytherapy system is shown generally at 20 in FIG. 1. The system 20 includes a TRUS transducer 24 coupled to a motor assembly 28 that operates to control the longitudinal movement and rotation of the TRUS transducer 24. The TRUS transducer 24 is also coupled to a conventional ultrasound machine 32 for displaying image data as it is captured by the TRUS transducer 24. A video frame-grabber 36 is connected to the ultrasound machine 32 to capture image data therefrom. The video frame-grabber 36 preferably operates at 30 Hz or greater to provide rapidly updated ultrasound images.

A computer 40 is connected to the video frame-grabber 36 and retrieves ultrasound images from the memory of the video frame-grabber 36. The computer 40 is coupled to a mover controller module ("MCM") 44 that is coupled to and controls the motor assembly 28. The computer 40 is also connected to the TRUS transducer 24. Further, the computer 40 is connected to a robot 48 having a needle driving assembly 52 and needle guide 56 for controlling movement of a needle 60. The needle 60 is used to deliver therapy to a prostate 64 of a patient. The robot 48 receives needle control commands from and transmits needle position information to the computer 40.

The TRUS transducer 24 is operable to continuously capture radial 2D US images over a radial operational scan range. The MCM 44 which controls the TRUS transducer 24 is in communication with the computer 40 to receive TRUS control commands via the serial port of the computer 40. The TRUS control commands direct the MCM 44 to control the motor assembly 28. In turn, the motor assembly 28 controls the longitudinal movement and rotation of the TRUS transducer 24. Additionally, the TRUS control commands control the timing of image data capture of the TRUS transducer 24.

The needle driving assembly 52 includes a robotic arm with six degrees-of-freedom. The degrees-of-freedom correspond to translations of the needle 60 in three dimensions and rotation of the needle 60 about three orthogonal axes. In this manner, the needle 60 can be positioned in a wide variety of orientations. The needle guide 56 is a one-holed template that is used to stabilize lateral movement of the needle 60 during insertion.

The computer 40 is a personal computer having a processor that executes software for performing 3D image acquisition, reconstruction and display. The processor also executes software for determining dosimetry of a selected therapy, and for controlling the TRUS transducer 24 and the robot 48. The software executed by the processor includes TRUS controller software, positioning software, imaging software, 3D visualization software and dose planning software.

The TRUS controller software generates TRUS control commands for directing the MCM 44, thereby controlling the longitudinal and rotational movement and the image data acquisition timing of the TRUS transducer 24.

The positioning software generates needle control commands to control movement of the needle driving assembly 52 of the robot 48. The positioning software can direct the robotic arm to move in terms of world or tool coordinate systems. The world coordinate system is fixed to the ground, whereas the tool coordinate system is fixed to the robotic arm. Further, the positioning software can direct the needle driving assembly 52 to control the longitudinal movement of the needle 60.

The imaging software captures, analyzes and processes ultrasound images using the image data retrieved from the memory of the video frame-grabber 36. The positioning software provides needle position information using the selected coordinate system. In turn, the imaging software directs the TRUS controller software to vary the operation of the TRUS transducer 24 as will be explained.

The 3D visualization software renders 3D images to be presented on a display (not shown) of the computer 40 using the image data captured and processed by the imaging software. In particular, the 3D visualization software generates three orthogonal views of the target volume: two that are co-planar to the needle 60 and a third that generally bisects the needle 60.

The dose planning software performs precise image-based needle trajectory planning. In addition, the dose planning software provides planned needle trajectory information to the 3D visualization software so that the planned needle trajectory can be overlaid atop the US images on the display. The actual needle trajectory can then be viewed in relation to the planned needle trajectory. The dose planning software can also receive and process the US images from the imaging software and dynamically re-determine the dosimetry based on the actual needle trajectory and seed implantation locations.

Prior to use, the positioning software controlling movement of the robot 48, the needle driving assembly 52 and, thus, the needle 60, and the imaging software are calibrated. During calibration, the mapping between the selected coordinate system of the positioning software and the 3D TRUS image coordinate system is determined and synchronized. In this manner, the imaging software can be made aware of the expected position of the needle 60 before detection via imaging.

By unifying the robot 48, the TRUS transducer 24 and the 3D TRUS image coordinate systems, the position of the template hole of the needle guide 56 can be accurately related to the 3D TRUS image coordinate system, allowing accurate and consistent insertion of the needle via the hole into a targeted position in a prostate along various trajectories including oblique ones. Further, the operation of the TRUS transducer 24 can be varied to focus its attention on the expected position of the needle 60.

Figure 2:
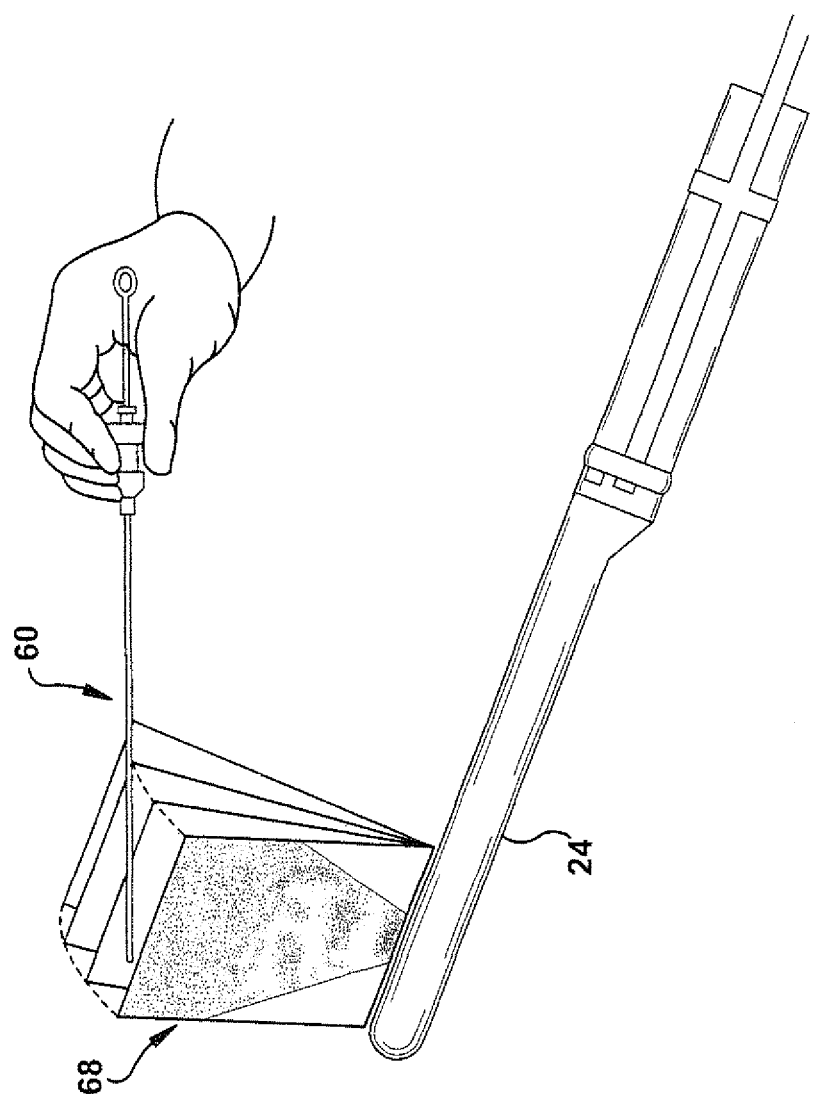
FIG. 2 shows a three-dimensional ("3D") TRUS transducer forming part of the ultrasound imaging system of FIG. 1 capturing a set of 2D US images of a needle.

FIG. 2 shows the 3D TRUS transducer 24 capturing a set of 2D US images. As the TRUS transducer 24 is rotated by the MOM 44, it captures image data to generate a series of 2D images 68. The 2D images 68 are captured at generally regular intervals during rotation of the TRUS transducer 24. Initially, the TRUS transducer 24 captures a 2D image 68 every one degree of rotation and rotates through 100 degrees, thereby capturing one hundred and one 2D images 68. The captured 2D images 68 are fanned radially in relation to the TRUS transducer 24. The needle 60 is shown having an oblique trajectory in relation to the 2D images 68, and intersects two or more of the 2D images 68.

As will be understood, insertion of the needle 60 along an oblique trajectory results in the intersection of the 2D TRUS image planes. As a result, the needle 60 only appears as a point in the captured 2D US images.

Figure 3:
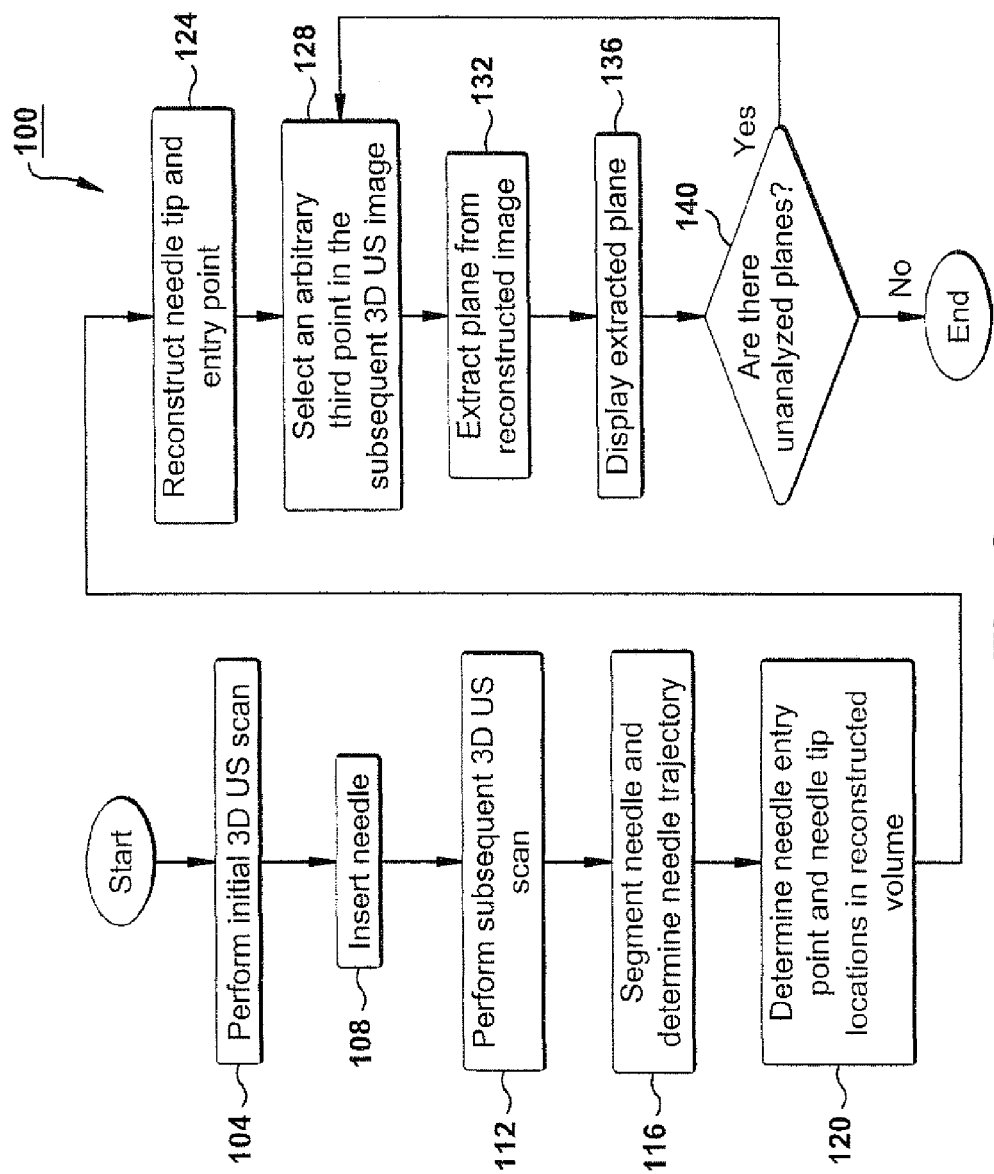
FIG. 3 is a flow chart of the general method of operation of the system of FIG. 1.

A near real-time method 100 for identification, segmentation and tracking of needles will now be described with reference to FIG. 3. The method 100 enables the tracking of the needle 60 even if the needle 60 is not coplanar and, thus, exits a 2D US image plane as a result of an oblique insertion. The method can also be used for the identification, segmentation and tracking of needles if they are completely contained in a 2D US image plane. To perform near real-time needle segmentation for an oblique trajectory, capture of two 3D US images is required. A 3D US image is comprised of two or more 2D US images that are offset. Note, that if the needle 60 is coplanar with a 2D US image, then two 2D US images can generally be used, but the procedure is unchanged.

The initial 3D US image is obtained by scanning the prostate (tissue) to obtain a set of 2D US images before the needle is inserted. This 3D US image establishes a baseline or control against which other images will be compared. A subsequent 3D US image is then acquired by scanning only the region containing the needle. It is to be understood that the second 3D US image may not be, in fact, the next 3D US image captured after the first, but refers to any subsequently-captured 3D US image. The method, as described, is used to identify, segment and track the needle in each subsequent 3D US image captured after the first 3D US image is captured. Each new 3D US image is compared to the initial image to identify the position of the needle at that time.

The method 100 commences with the performance of an initial 3D US scan (step 104). The needle 60 is then inserted into the target volume (step 108). Next, a subsequent 3D US scan is performed (step 112). The needle 60 is segmented to distinguish its location using the initial and subsequent 3D US images (step 116). The needle trajectory is then determined (step 120). Once the needle trajectory has been determined, the needle tip and needle entry point locations within the reconstructed volume are determined (step 124). The needle tip and entry point locations are then reconstructed (step 128). An arbitrary third point in the target volume is selected (step 132). The plane defined by the needle tip and entry points and the arbitrary third point is extracted from the reconstructed 3D image (step 136). Next, the extracted plane is displayed (step 140). It is then determined if there are any remaining unanalyzed planes (step 144). If there are, the method 100 returns to step 132, at which another arbitrary point is selected. If, instead, all of the desired planes have been analyzed, the method 100 ends.

During the performance of the initial 3D US scan at step 104, the MCM 44 and motor assembly 28 causes the TRUS transducer 24 to rotate about its long axis over about 100 degrees while image data corresponding to 2D US images is captured at one degree intervals. The image data corresponding to the 2D US images is then transmitted to the computer 40 to be digitized by the video frame grabber 36 and registered by the imaging software.

The acquired 2D US images are processed by the imaging software as they are collected. The 2D US images correspond to planes radially extending from the central axis of rotation of the TRUS transducer 24. Accordingly, the 3D volume is reconstructed by translating and rotating the 2D US images with respect to one another. The reconstructed 3D volume consists of an array of voxels, or 3D pixels. The voxels are typically cubic (but can also be rhomboidal) and are arranged according to a 3D Cartesian system. Each voxel is assigned a greyscale-level value based on the greyscale-level values of the pixels in the translated 2D images adjacent to it.

Figure 4:
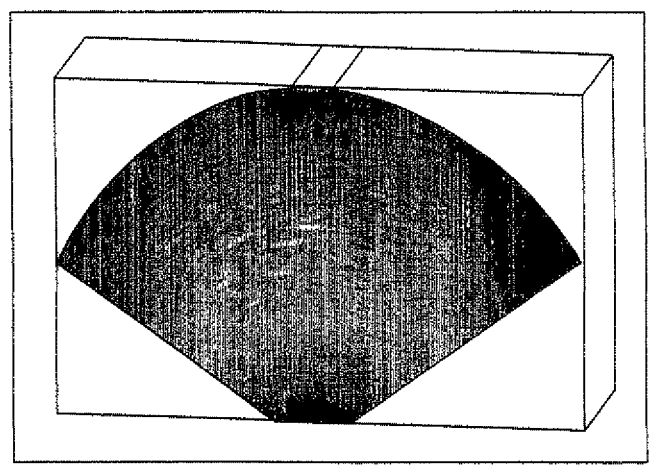
FIG. 4 shows a reconstructed 3D image generated from 2D ultrasound images captured by the TRUS transducer shown in FIG. 2.

FIG. 4 illustrates a 3D US image reconstructed from the set of 2D US images. As can be seen, the 3D US image has a fan profile corresponding to the volume imaged by the TRUS transducer 24. The acquired 2D US images are reconstructed into a 3D US image by the imaging software. The 3D visualization software then generates a view of the 3D US image, and provides a multi-planar 3D display and volume rendering, as well as an extensive set of measurement tools. The 3D US image is then presented for viewing on the display of the computer 40. As each new 2D US image is acquired by the TRUS transducer 24 during its rotation, the 3D visualization software dynamically updates the 3D image presented on the display.

During the performance of the subsequent 3D US scan at step 112, a region of interest is identified, and the ultrasound imaging system 20 is focused on a segment of an operational scan range of the TRUS transducer encompassing the region of interest in a target volume. In particular, the TRUS transducer is focused on the segment to capture images of the expected position of the needle 60. While the expected position of the needle 60 in the 3D US images can be determined based on the needle position coordinates provided by the positioning software, needle deviations in the 3D US images can occur for a number of reasons. These include slight bending of the needle 60 as it is inserted and shifting in the target volume. By obtaining a new 3D US image, the actual position of the needle 60 can be more precisely determined.

Figure 5:
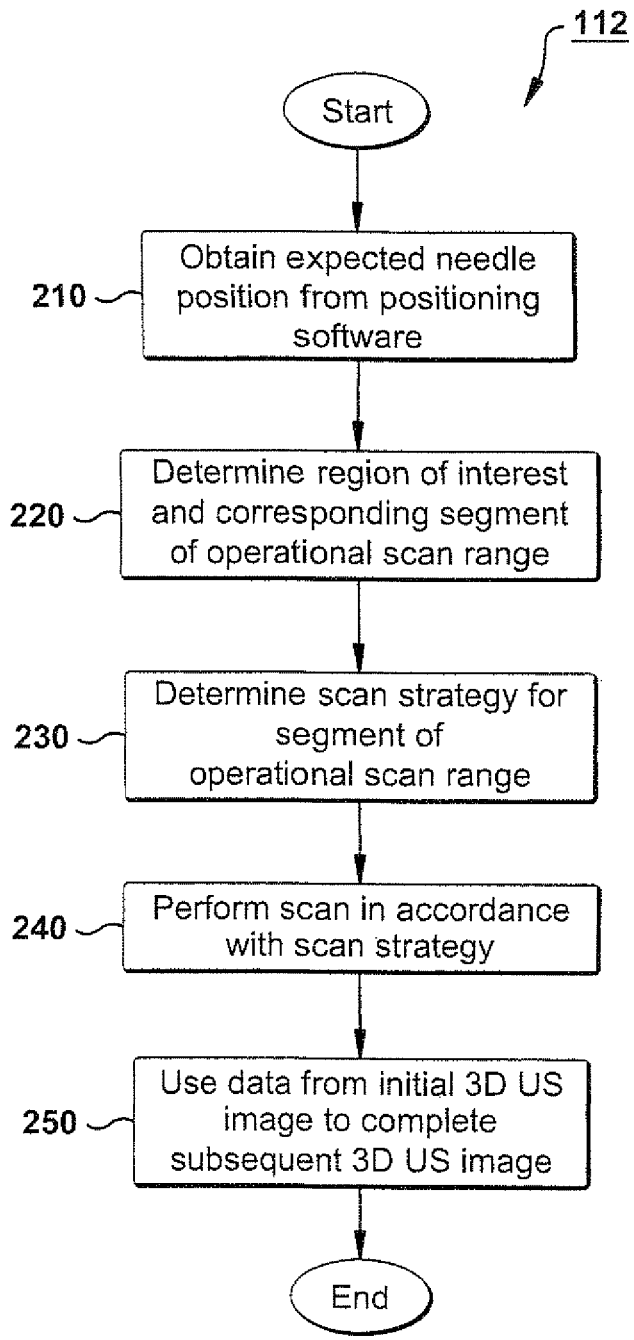
FIG. 5 is a flow chart illustrating the method of performing a subsequent 3D US scan.

FIG. 5 better illustrates the performance of the subsequent 3D US scan. The expected needle position is obtained from the positioning software (step 210). The region of interest is determined based on the expected position of the needle, and a corresponding segment of the operational scan range of the TRUS transducer 24 is determined (step 220). Next, a scan strategy for the segment of the operational scan range is determined (step 230). In determining the scan strategy for the segment of the operational scan range at step 230, the positions of 2D US images to be acquired is determined. In particular, a set of 2D US images are planned at one-half degree intervals along the angular width of the scan region of interest. A scan is then performed in accordance with the scan strategy (step 240). Data from the initial 3D US image is then used to complete the 3D US image (step 250).

During the determination of the region of interest at step 220, the region of interest is selected to include the expected needle position obtained during step 210. Where the needle has yet to be inserted/detected, the region of interest is defined to be an area around the expected needle entry point. If, instead, the needle was at least partially inserted/detected at the time of the last 3D US scan, the region of interest is determined to include the original needle position plus a distance along the needle trajectory beyond the needle tip as will be described.

The region of interest is then reverse-mapped onto the operating coordinates of the TRUS transducer 24 and is used to determine a segment of the operational scan range of the TRUS transducer 24 that encompasses the region of interest at step 230. In particular, the segment of the operational scan range is selected to correspond to an angular sector of the operational scan range of the TRUS transducer 24 that encompasses the region of interest. Where the needle is inserted along an oblique trajectory and, consequently, intersects a number of 2D US images at points, the angular width of the sector is selected to sufficiently cover the region of interest plus five degrees of rotation to cover the distance along the needle trajectory beyond the needle tip.

Figure 6:
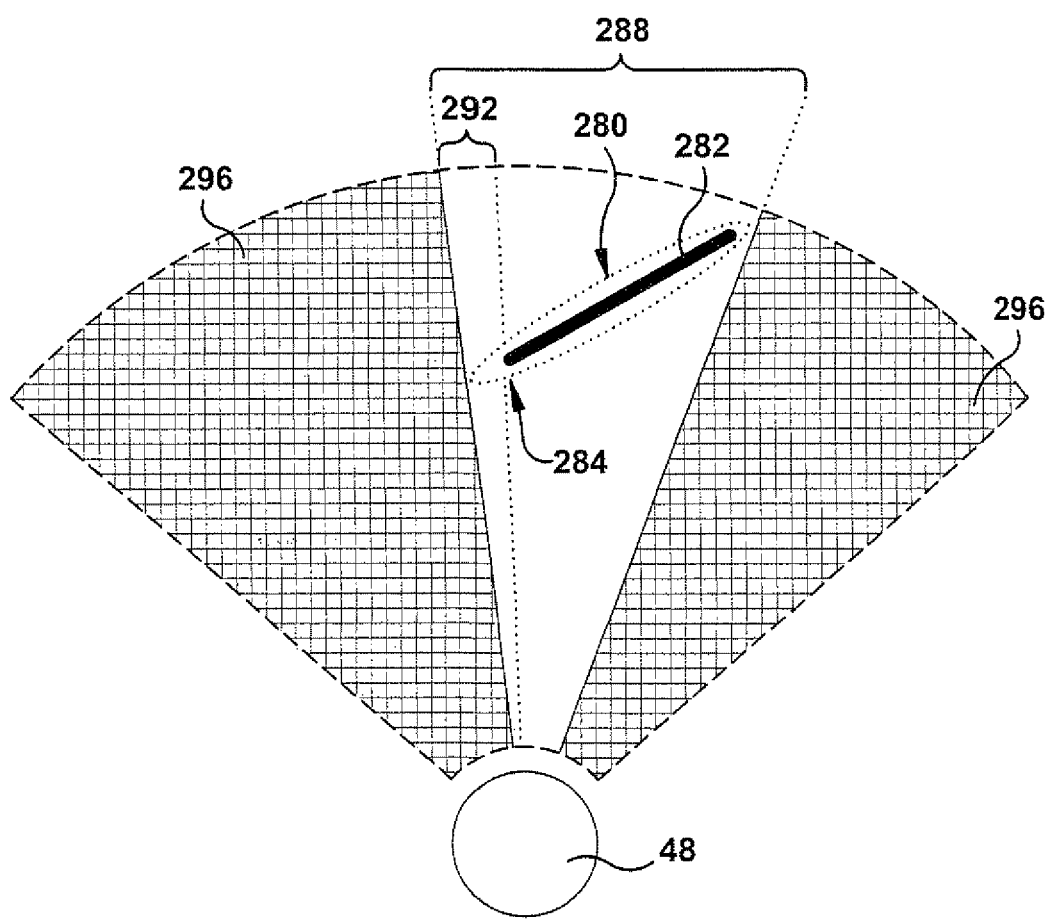
FIG. 6 is a sectional view of a scan range corresponding to a region of interest determined using the method of FIG. 5.

FIG. 6 is an end-view of the TRUS transducer 24 and the segment of the operational scan range selected during step 220 for the needle when it is inserted along an oblique trajectory. A region of interest 280 encompasses an expected needle position 282 and extends a distance past the expected needle tip position 284. A segment of the operational scan range 288 corresponding to the sector encompasses the region of interest 280. The segment of the operational scan range 288 includes a five-degree margin 292 to capture the region of interest extending along the needle trajectory beyond the expected needle tip position 284. Two background areas 296 of the operational scan range of the TRUS transducer 24 flank either side of the sector.

During the completion of the subsequent 3D US image at step 250, data from the initial 3D US image is used to fill in the background areas. As the scan strategy can exclude the capture of some or all image data from the background areas, image data from the initial 3D US scan is used to fill in any image data required in the subsequent 3D US image. The image data in the background areas is not expected to change and can, thus, be borrowed from the initial 3D US image.

By modifying the behavior of the TRUS transducer 24 to focus on the region of interest, more detailed information can be captured around the tip of the needle 60 on a near real-time basis. Further, by reducing the scanning density for the other areas, the additional time required to scan the region of interest can be compensated for.

After the initial and subsequent 3D US scans have been completed, the needle 60 is segmented at step 116. The subsequent 3D US image is compared to the initial 3D US image, and the needle position within the subsequent 3D US image, including the needle tip and entry point location, is determined. The needle 60 will show up as voxels with a greyscale-level change that exceeds a threshold value between the initial and subsequent 3D US images. There can be, however, other voxels with a greyscale-level change that exceeds the threshold value that do not, in fact, represent the needle, but may represent, for example, calcifications in the prostate. In order to permit better identification of the actual needle, the system 20 attempts to identify and discard these other voxels.

Figure 7:
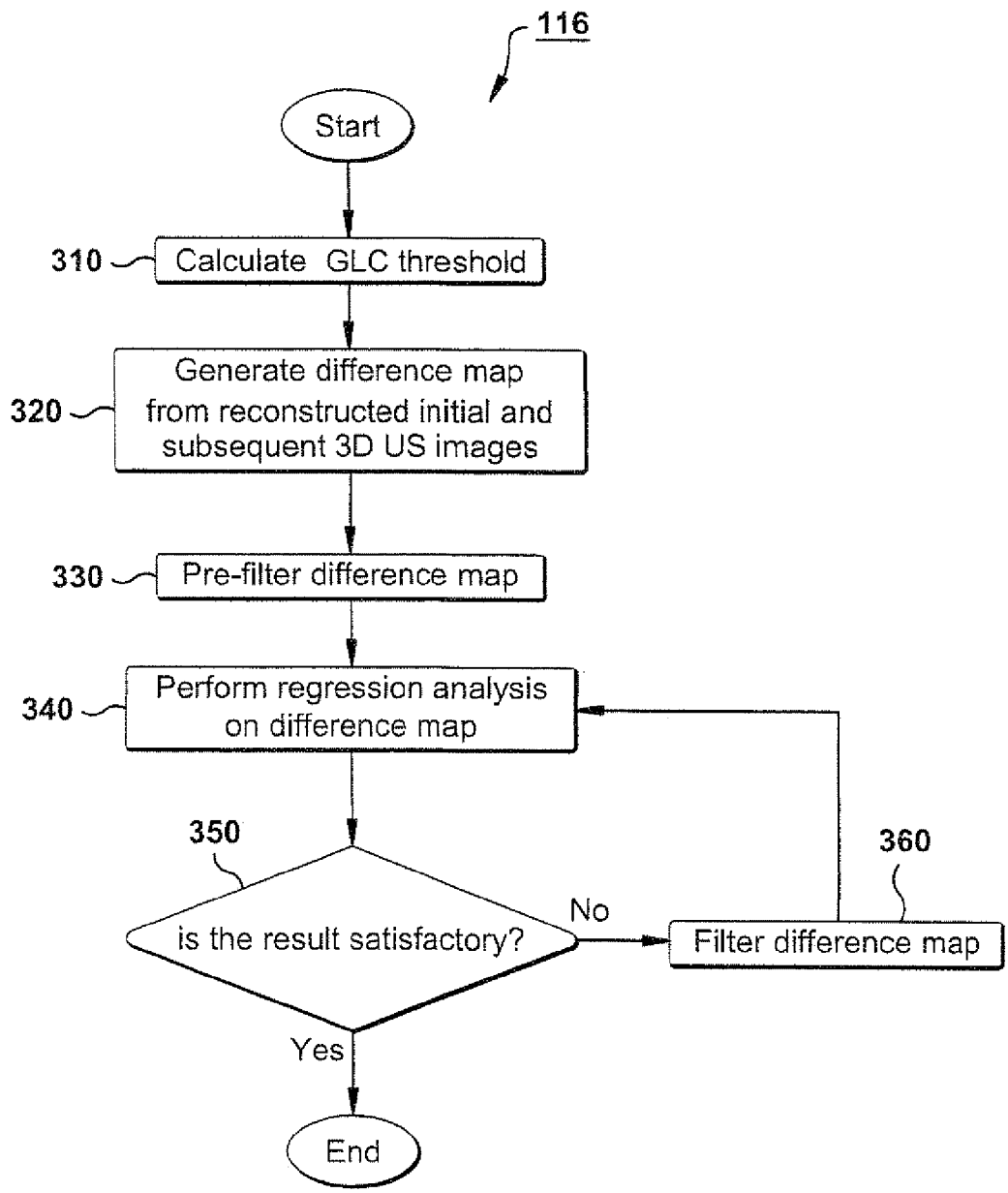
FIG. 7 is a flow chart that illustrates the method of segmenting a needle.

FIG. 7 better illustrates the method of needle segmentation at step 116. The method commences with the calculation of a greyscale-level change threshold (step 310). A difference map is then generated from the initial and subsequent 3D US images (step 320). Next, the difference map is pre-filtered (step 330). Regression analysis is performed on the difference map to identify the needle (step 340). The result of the regression analysis is then analyzed to determine if it is satisfactory (step 350). If the results are determined to be unsatisfactory, the difference map is filtered (step 360), and the method returns to step 340, where regression analysis is again performed on the filtered image. The filtering of the difference map and the regression analysis is repeated until all of the voxels in the difference map are within a prescribed range from the regression line. As the filtering removes outlying voxels, their effect on the linear regression is removed, thereby allowing the needle trajectory to be more accurately estimated. Reiterative filtration of the difference map is performed to obtain a desired level of confidence in the estimated needle trajectory. Once the result of the regression analysis is deemed to be satisfactory at step 350, the method ends.

Figure 8:
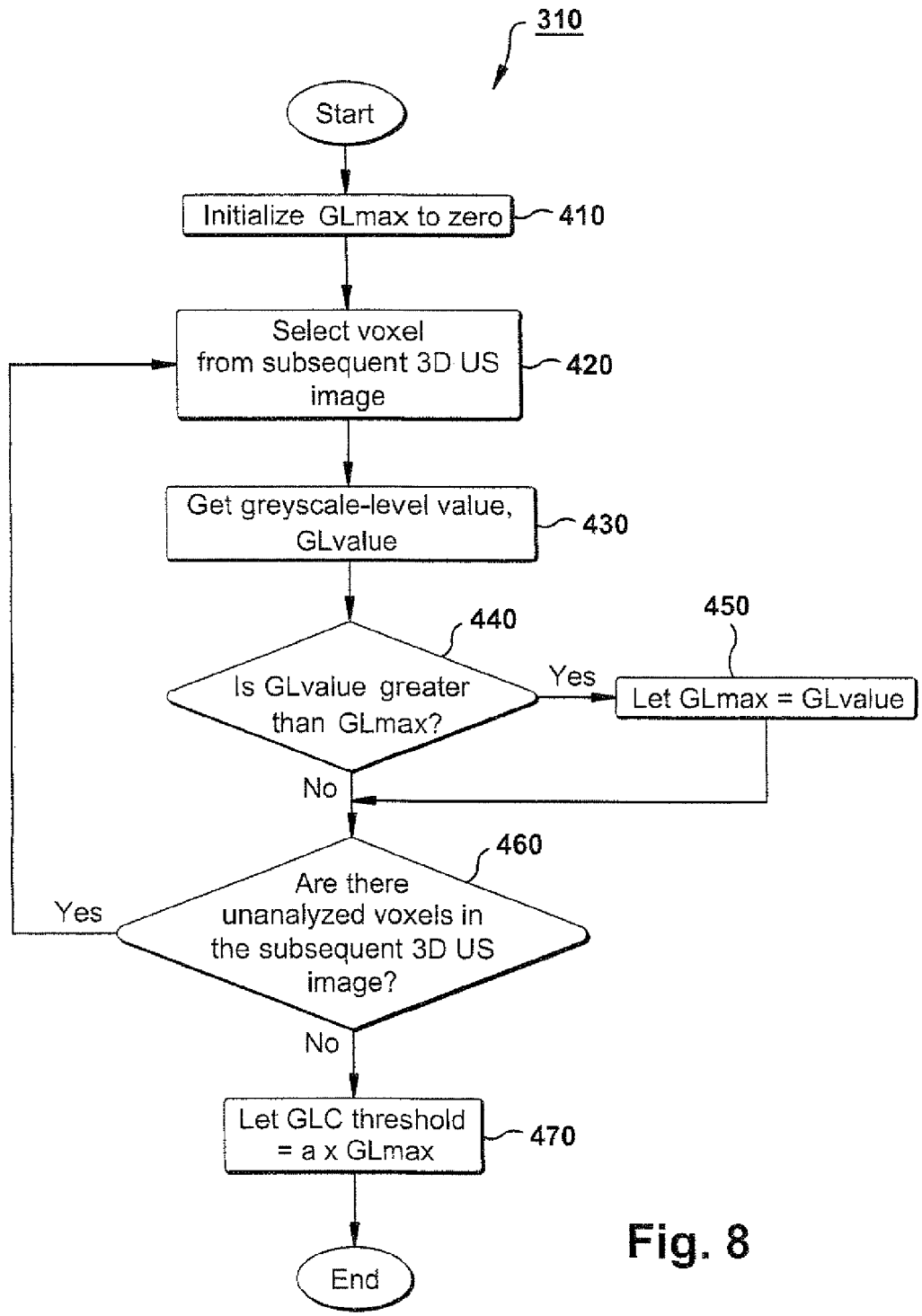
FIG. 8 is a flow chart that illustrates the method of determining the greyscale-level change threshold.

FIG. 8 better illustrates the calculation of the greyscale-level change threshold at step 310. A greyscale-level change threshold value, GLC threshold, is used to reduce the number of voxels to be analyzed in the 3D US images and to obtain candidate needle voxels. To determine the threshold value, the maximum greyscale-level value, $GL_{max}$, in the subsequent 3D US image is first determined by examining each voxel in the image, and then $GL_{max}$ is multiplied by a constant.

The calculation of GLC threshold commences with the setting of $GL_{max}$ to zero (step 410). A voxel is then selected from the subsequent 3D US image (step 420). The greyscale-level value, $GL_{value}$, of the selected voxel is determined (step 430). The greyscale-level value of the selected voxel, $GL_{value}$, is then compared to the maximum greyscale-level value, $GL_{max}$ (step 440). If the greyscale-level value of the selected voxel, $GL_{value}$, is greater than the maximum greyscale-level value, $GL_{max}$, the value of $GL_{max}$ is set to $GL_{value}$ (step 450). It is then determined whether there are any unanalyzed voxels remaining in the subsequent 3D US image (step 460). If there are, the method returns to step 420, where another voxel is selected from the subsequent 3D US image. If, instead, it is determined at step 460 that there are no remaining unanalyzed voxels in the subsequent 3D US image, the greyscale-level change threshold value is calculated as follows:

$$GLC\ threshold = a \times GL_{max} \quad (\text{Eq. 1})$$

where $0 < a < 1$. A value for a of 0.5 provides desirable results.

Figure 9:
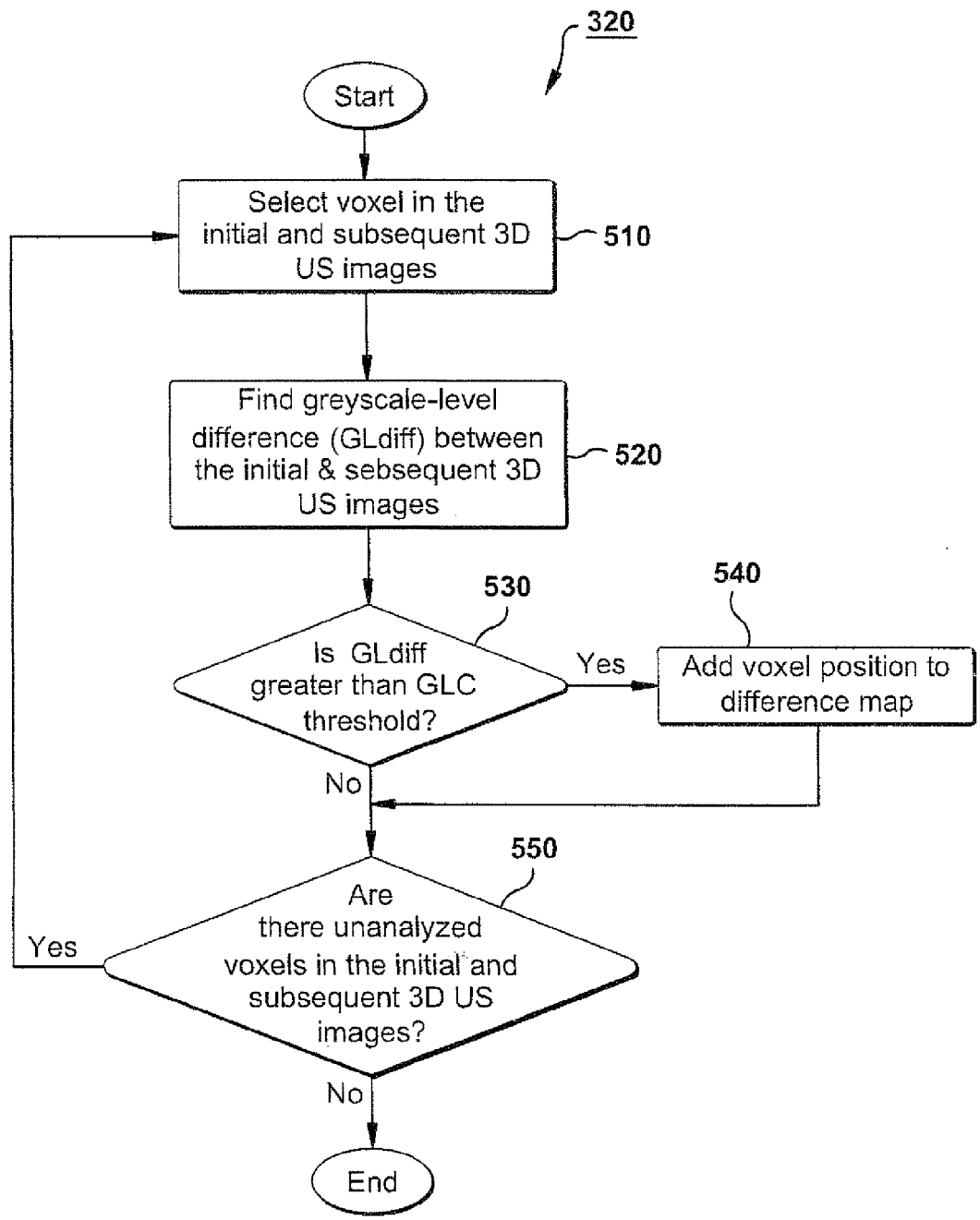
FIG. 9 is a flow chart that illustrates the method of generating a difference map.

FIG. 9 better illustrates the generation of a difference map during step 320 using the threshold calculated during step 310. The difference map is a registry of candidate needle voxels that represent an area of the same size as the initial and subsequent 3D US images. Initially, the greyscale-level value of each voxel in the initial 3D US image is compared to that of its counterpart in the subsequent 3D US image, and the difference is determined:

$$GLC(i,j,k) = postGL(i,j,k) - preGL(i,j,k) \quad (\text{Eq. 2})$$

where preGL(i,j,k) and postGL(i,j,k) are the greyscale-level values of voxels at location (i,j,k) in the initial and subsequent 3D US images respectively, and GLC(i,j,k) is the greyscale-level change.

Those voxels in the subsequent 3D US image whose greyscale-level values exceed those of their counterpart in the initial 3D US image are deemed to have changed significantly and are registered in the difference map. That is, $$(i_m,j_m,k_m) \in 3D\ DM,\ \text{where}\ GLC(i_m,j_m,k_m) > GLC\ threshold \quad (\text{Eq. 3})$$

for m=1, 2, . . . , n, where n is the number of points included in the 3D difference map. The remaining voxels having greyscale-level values that do not exceed those of their counterpart in the initial 3D US image are deemed to have changed insignificantly and are not added to the difference map.

The method of generating the difference map begins with the selection of a voxel in the subsequent 3D US image and its counterpart in the initial 3D US image (step 510). The greyscale-level difference, GLdiff, between the voxels of the initial and subsequent 3D US images is found (step 520). The greyscale-level difference, GLdiff, is compared to the greyscale-level change threshold, GLC threshold, to determine if it exceeds it (step 530). If it is determined that the greyscale-level difference, GLdiff, exceeds the greyscale-level change threshold, GLC threshold, the position of the voxel is added to the difference map (step 540). It is then determined whether there are any remaining unanalyzed voxels in the initial and subsequent 3D US images (step 550). If it is determined that there are unanalyzed voxels remaining in the initial and subsequent 3D US images, the method returns to step 510, where another pair of voxels is selected for analysis. If, instead, it is determined that all of the voxels in the initial and subsequent 3D US images have been analyzed, the method of generating the difference map ends.

During pre-filtration of the difference map at step 330, voxels registered in the difference map are analyzed to remove any voxels that are deemed to be noise. In the system 20, the 3D image is advantageously reconstructed on demand and, therefore, access to the original acquired image data is available.

Voxels are identified and analyzed to determine whether they correspond to a characteristic of the needle. Since the image of the needle is expected to extend along the 3D scanning direction, voxels representing the needle are assumed to be generally adjacent each other along this direction. Other voxels in the difference map that are more than a pre-determined distance along this direction from other voxels are deemed to be noise and removed. That is, assuming that k is the direction along which the needle is expected to extend, voxels are removed from the difference map as follows:

$$(i_m, j_m, k_m) \notin 3D\ DM, \quad (\text{Eq. 4})$$

$$\text{where}\ \bigcup_{m=1}^{P} GLC(i_m, j_m, k_m \pm s) < GLC\ threshold$$

where, s=1, 2, . . . , $P/2$, and P is the number of voxels surrounding voxel $(i_m, j_m, k_m)$ in the k-direction. A value for P of 4 provides desirable results.

Figure 10A:
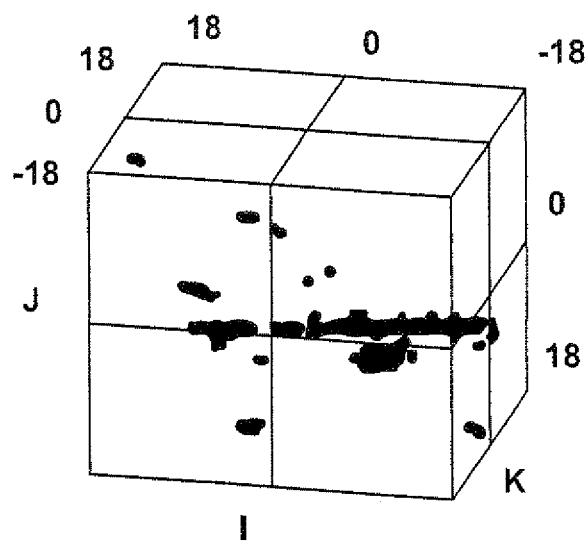
FIGS. 10a and 10b show the difference map generated using the method of FIG. 9 before and after pre-filtration respectively.
Figure 10B:
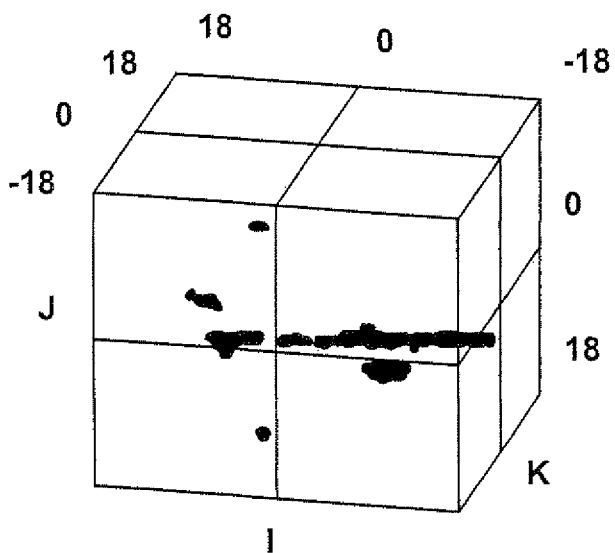

FIGS. 10a and 10b show the difference map prior to and after pre-filtration respectively. As can be seen, spurious voxels not occurring in clusters extending along the same path as the needle are removed during pre-filtration.

Once the difference map has been pre-filtered, regression analysis is performed on the difference map at step 340. During this analysis, a line is fit to the voxels in the difference map using linear regression analysis. The equation of the line determined from the difference map using linear regression analysis provides the estimated trajectory for the needle.

Figure 11:
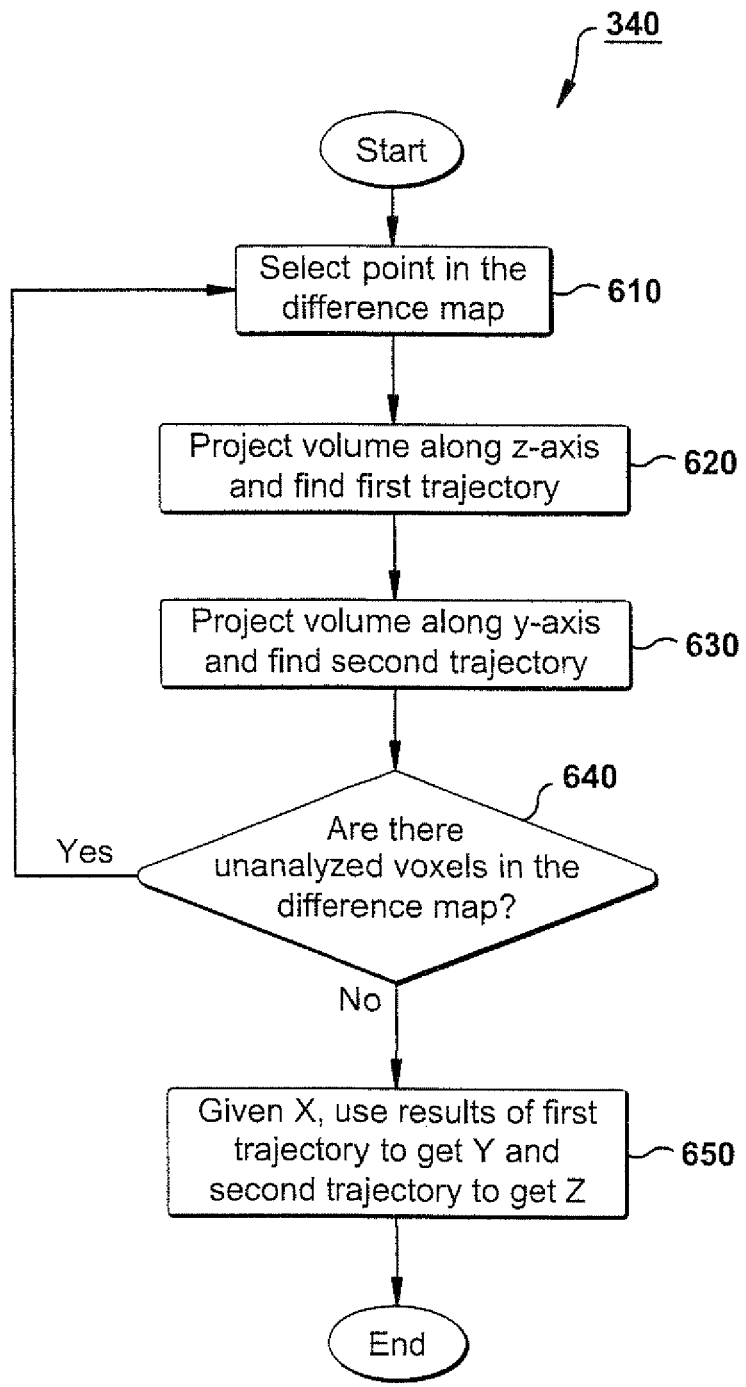
FIG. 11 is a flow chart that illustrates the method of performing regression analysis.

FIG. 11 better illustrates the performance of the regression analysis on the difference map at step 340. A voxel registered in the difference map is selected (step 610). The volume is projected along the z-axis to find a first trajectory (step 620). Next, the volume is projected along the y-axis to find a second trajectory (step 630). It is then determined if there are any unanalyzed voxels in the difference map (step 640). If it is determined that there are unanalyzed voxels in the difference map, the method returns to step 610, where another voxel is selected in the difference map for analysis. If, instead, all of the voxels in the difference map have been analyzed, the results of the first trajectory are used to obtain y and the results of the second trajectory are used to obtain z, given x (step 650). Once (x,y,z) has been determined, the method 240 ends.

If it is determined at step 350 that the linear regression is unsatisfactory, the difference map is filtered at step 360.

Figure 12:
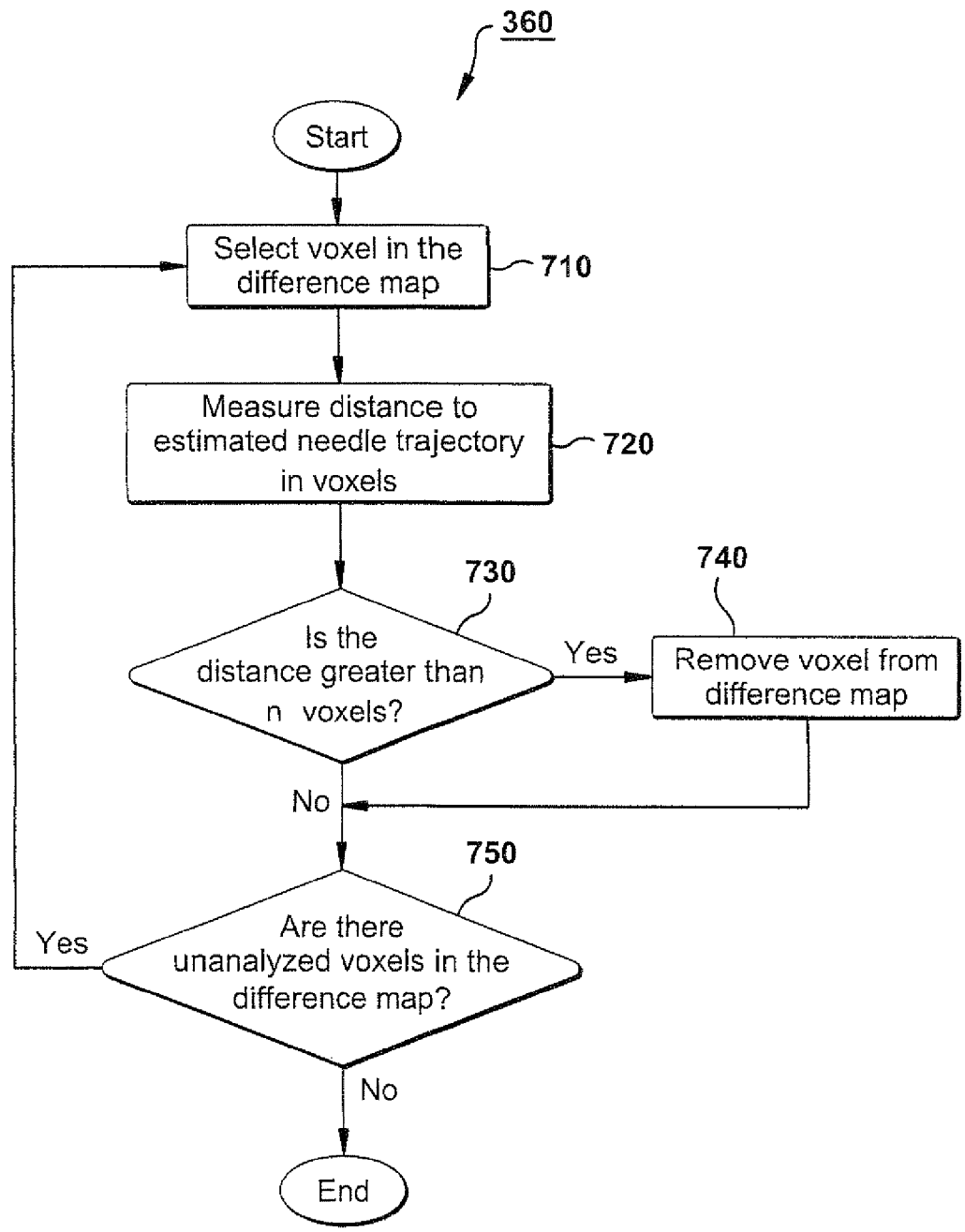
FIG. 12 is a flow chart that better illustrates the method of filtering the difference map.

FIG. 12 better illustrates the filtering of the difference map. During the filtering of the difference map, spurious voxels that are further than a predetermined distance from the estimated trajectory of the needle determined during step 340 are removed.

The method of filtering the difference map commences with the selection of a voxel in the difference map (step 710). The distance to the estimated needle trajectory is measured in voxels (step 720). A determination is then made as to whether the distance between the voxel and the estimated needle trajectory is greater than a pre-determined distance limit (step 730). It has been found that filtering out voxels further than five voxels in distance from the segmented needle trajectory provides desirable results. If the distance determined is greater than the pre-determined distance limit, the voxel is removed from the difference map (step 740). Then, it is determined if there are any unanalyzed voxels remaining in the difference map (step 750). If there are, the method returns to step 710, wherein another voxel in the difference map is selected for analysis. If, instead, all of the voxels in the difference map have been analyzed, the method of filtering the difference map ends.

Figure 13:
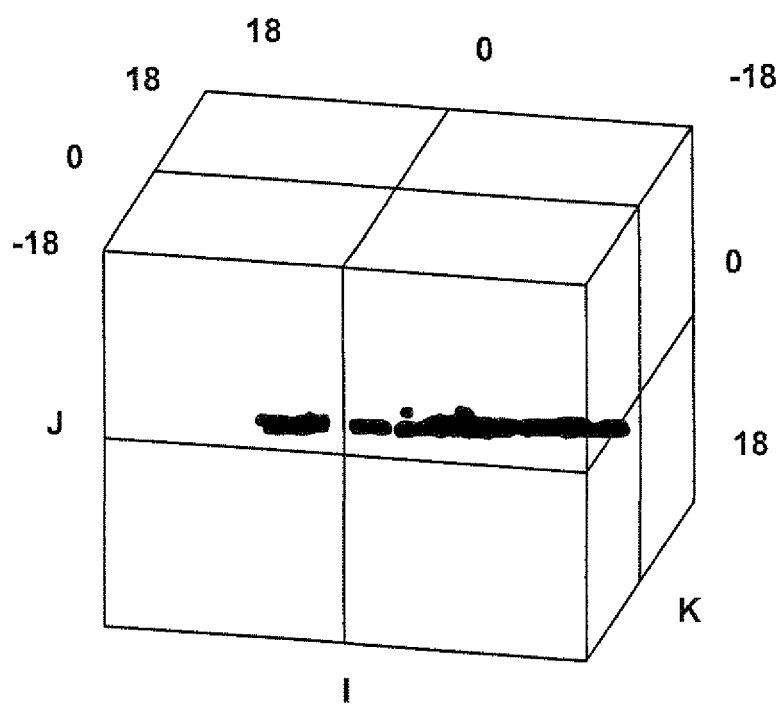
FIG. 13 shows the difference map of FIGS. 10a and 10b immediately prior to the performance of the final regression analysis.

FIG. 13 shows the difference map of FIGS. 10a and 10b after filtration at step 360 and immediately prior to the final regression calculation. As can be seen, the difference map is free of spurious voxels distant from the visible needle trajectory.

As mentioned previously, once the needle trajectory has been determined, the needle entry point and needle tip locations are reconstructed at step 124. The needle entry point is determined to be the intersection of the needle trajectory and the known entry plane. The needle tip is deemed to be the furthest needle voxel along the needle trajectory.

After the needle tip and entry point have been reconstructed, an arbitrary third point in the subsequent 3D US image is selected at step 128. To extract any plane containing the needle, the segmented needle entry point, needle tip point and a third point within the subsequent 3D US image are used to define a specific plane that is coplanar with the needle (i.e., contains the needle lengthwise). The location of the arbitrary point determines whether the plane will be sagital-oblique or coronal oblique. For a sagital-oblique plane, the arbitrary point is picked on a line going through the needle entry point and parallel to the y-axis. For a coronal-oblique plane, the arbitrary point is picked on a line going through the needle entry point and parallel to the x-axis.

The data occurring along the plane in the 3D US image is extracted at step 132 to permit generation of a 2D US image of the plane. In this way, the oblique saggital, coronal and transverse views with the needle highlighted can be extracted and displayed.

Once the plane is extracted, the 2D US image of the plane is presented on the display of the computer 40 at step 136. The location of the needle 60 in the 2D US image is demarcated using a colored line in the greyscale image to facilitate visual identification of the needle.

It is then determined whether there remain any unanalyzed planes at step 140. As three planes are displayed by the computer 40 at the same time, the process is repeated twice to obtain the other two planes. The first plane selected for analysis is the saggital plane and the other two planes are orthogonal to the first plane. If there are, the method returns to step 128, where another arbitrary point is selected to define another plane. Otherwise, the method 100 ends.

Figure 14A:
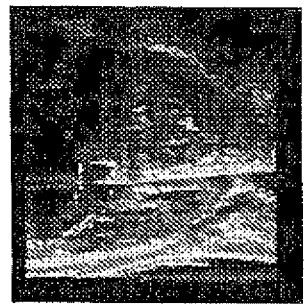
FIGS. 14a to 14c show various 2D US images generated using the ultrasound imaging system of FIG. 1.
Figure 14B:
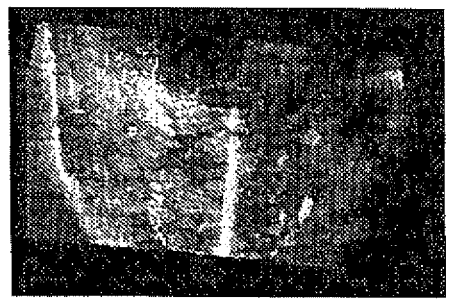
Figure 14C:
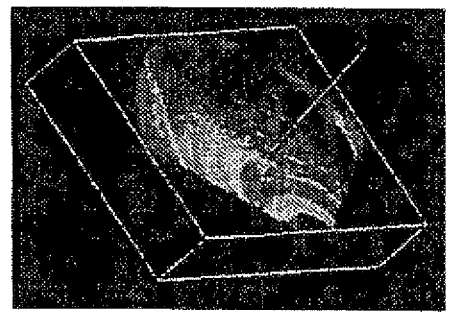

FIGS. 14a to 14c show a 2D US image obtained using the method 100 during a patient's prostate cryotherapy procedure, demonstrating that the needle can be tracked as it is being inserted and orthogonal views can be displayed for the user during the insertion procedure.

Evaluation

Experimental Apparatus

The accuracy and variability of the needle segmentation and tracking technique was tested using images acquired by scanning phantoms. Referring again to FIG. 1, the robot 48 shown was used to insert the needle 60 at known angles, including oblique trajectories with respect to the TRUS image plane.

The needle used in these experiments was a typical 18-gauge (i.e., 1.2 mm in diameter) prostate brachytherapy needle. The two US tissue-mimicking phantoms were made of agar, using a recipe developed by D. W. Ricky, P. A. Picot, D. C. Christopher, A. Fenster, *Ultrasound Medical Biology*, 27(8), 1025-1034, 2001, and chicken breast tissues. TRUS images were obtained using an 8558/S side-firing linear array transducer with a central frequency of 7.5 MHz, attached to a B-K Medical 2102 Hawk US machine (B-K, Denmark). The computer was a Pentium III personal computer equipped with a Matrox Meteor II video frame grabber for 30 Hz video image acquisition.

Algorithm Execution Time

Execution time is dependent on the 3D scanning angular interval and the extent of the region to be investigated. To evaluate the execution time of the disclosed method of needle segmentation the initial 3D US scan was performed, and then the needle was inserted. After needle insertion, the phantom was scanned again, and the needle was segmented. A software timer was used to measure the time elapsed during the execution of the segmentation.

Accuracy Test

To test the accuracy of the method, the robot was used to guide the needle insertion into the phantom at known angles. The angulation accuracy of the robot was evaluated to be 0.12±0.07 degrees.

First, the robot was used to guide the needle insertion along a trajectory parallel to the TRUS transducer 24, hereinafter referred to as the zero (0) degree orientation. Since the needle could be verified by observing the needle in the real-time 2D US image, this trajectory was assumed to be correct. As a result, oblique trajectory accuracy measurements could be made with respect to the zero degree trajectory. The positions of the needle tip and the needle entry point were then found for the zero degree trajectory using the method described above. The robot 48 was used to insert the needle at different angles (+5, +10, +15, −5, −10 and −15 degrees) with respect to the zero degree trajectory. For each insertion, the positions of the needle tip and the needle entry point were found. The corresponding segmented needle vectors through the needle entry point and needle tip were determined by using the following formula:

$$\cos\theta_{alg} = \frac{\vec{A}\cdot\vec{B}}{|\vec{A}||\vec{B}|} \quad\text{(Eq. 5)}$$

where $\vec{A}$ is the segmented needle vector for the zero degree trajectory; $\vec{B}$ is the segmented needle vector for the insertion at any other angle; $\theta_{alg}$ is the angle derived from the segmentation algorithm. The accuracy of the algorithm was evaluated by comparing $\theta_{alg}$ with the robot orientation angle $\theta_{rob}$. The error, $\epsilon_\theta$, was determined as follows:

$$\epsilon_\theta = |\theta_{alg} - \theta_{rob}| \quad\text{(Eq. 6)}$$

The accuracy test was repeated with a chicken tissue phantom, and the accuracy was again determined using Equations 5 and 6. For the agar phantoms, five groups of tests were performed to evaluate the algorithm execution time and accuracy. Each group consisted of seven insertions; i.e., insertion at 0, +5, +10, +15, −5, −10 and −15 degrees. The mean error as a function of insertion angle, $\epsilon_\theta$, was calculated as follows:

$$\varepsilon_\theta = \frac{\sum_{i=1}^{5} |(\theta_{alg})_i - (\theta_{rob})_i|}{5} \quad \text{(Eq. 7)}$$

Results and Conclusion

The following table presents the evaluation results. In the chicken tissue phantom, the average execution time was 0.13±0.01 seconds, and the average angulation error was 0.54±0.16 degrees. In agar phantoms, the average execution time was 0.12±0.01 seconds, and the average angulation error was 0.58±0.36 degrees. The results shown below also demonstrate that the insertion error does not significantly depend on insertion angle.

|   |                      | Angle (degrees) |      |      |      |      |      |
|---|----------------------|-----------------|------|------|------|------|------|
|   |                      | −15             | −10  | −5   | +5   | +10  | +15  |
| 1 | Time (seconds)       | 0.13            | 0.11 | 0.12 | 0.12 | 0.12 | 0.14 |
|   | Accuracy (degrees)   | 0.50            | 0.51 | 0.43 | 0.37 | 0.74 | 0.74 |
| 2 | Time (seconds)       | 0.12            | 0.12 | 0.12 | 0.11 | 0.12 | 0.13 |
|   | Accuracy (degrees)   | 0.30            | 0.71 | 0.48 | 0.68 | 0.42 | 0.86 |

In 3D US images, needle voxels generally have high greyscale-level values. However, due to specular reflection, some background structures may also appear to have high greyscale-level values. This increases the difficulty in automatic needle segmentation in a US image using greyscale-level information directly. As US images suffer from low contrast, signal loss due to shadowing, refraction and reverberation artifacts, the greyscale-level change detection technique of the disclosed embodiment of the invention appears to be quite robust. In addition, since the needle is segmented from a difference map, complex backgrounds can be ignored to simplify calculations and accuracy.

In conclusion, a greyscale-level change detection technique has been developed and its feasibility has been tested for near real-time oblique needle segmentation to be used in 3D US-guided and robot-aided prostate brachytherapy. The results show that the segmentation method works well in agar and chicken tissue phantoms. In addition, the approach has also been tested during several prostate cryotherapy procedures with positive results.

Alternative Methods of Defining the Region of Interest and Scan Strategies

A number of alternative methods for defining the region of interest and scan strategies have been explored for use with the system 20. In a first alternative, the region of interest is defined to include only a set length of the needle from the tip plus a pre-determined distance beyond the needle tip along the needle trajectory. For example, the region of interest can be defined to include a one-half-inch length of the needle measured from its tip and an area one-half inch along its trajectory beyond the needle tip. The scan strategy then is selected to capture 2D US images at one-half degree intervals along the angular width of the segment of the operational scan range of the transducer of the ultrasound imaging system encompassing the region of interest. As the needle is further inserted into the target volume, the region of interest roams with the needle tip. Using this approach, 2D US images can be rapidly captured and updated to provide accurate information about the position of the needle tip.

In another alternative method for defining the region of interest and scan strategy, the region of interest is defined to include an area of expected activity of a one-half-inch length of the needle measured from its tip and an area one-half inch along its trajectory beyond the needle tip. This area of expected activity generally allows the new position of the needle to be determined when compared to previous images. A scan strategy can then be selected to scan a segment of the operational scan range of the transducer of the ultrasound imaging system encompassing the region of interest using a fine scan density, and other areas using a coarse scan density. By selecting a relatively high scan density for the subset of the operational scan range of the transducer of the ultrasound imaging system and a relatively low scan density for other scan areas (e.g. one 2D US image every one-half degree interval in the region of interest, and every one-and-one-half degree interval outside the region of interest), detailed information about the region of interest can be obtained while still capturing a desired minimum level of detail about other areas.

Where the needle has yet to be detected, and information regarding the expected needle entry point is available, the region of interest can be defined to include an area surrounding the expected needle entry point.

Where the needle is not determined to be present in the region of interest, additional 2D images can be acquired to locate the needle.

Other alternative methods for defining the region of interest and scan strategy and combinations thereof will occur to those skilled in the art.

While the method of registering the position of an object moving in a target volume in an ultrasound imaging system and the method of imaging using an ultrasound imaging system have been described with specificity to a rotational US scanning method, other types of scanning methods will occur to those of skill in the art. For example, the same approach can be used with a linear US scanning method. In addition, the segmentation method can be applied equally well to 3D US images reconstructed using the linear scanning geometry, but acquired using rotational 3D scanning geometry such as that used in prostate imaging.

The linear regression analysis approach for determining the needle trajectory from the difference map was selected as it requires relatively low processing power. A person of skill in the art, however, will appreciate that any method of determining the needle trajectory given the difference map can be used. For example, the well-known Hough Transform technique can be employed. The Hough Transform technique requires higher computational power than the linear regression approach, but this can be ignored where such processing power is available.

While a specific method of determining the GLC threshold was disclosed, other methods of determining the GLC threshold will occur to those skilled in the art. For example, a histogram of the greyscale-level values in the 3D US image can be generated and then analyzed to determine the regions of the histogram that most likely correspond to the background and to the needle. The analysis can be based on the statistical distribution of the greyscale-level values due to the acoustic scattering of the tissue and the statistical distribution of the specular reflection of the needle.

In addition to 3D applications, difference maps can be used to register movement in a single 2D plane. In this case, the difference map could represent a 2D plane and register differences between two 2D images.

While, in the above-described embodiment, the expected needle position from the positioning software was used to determine the region of interest thereby to modify the scanning behavior of the TRUS transducer 24, one or more previous images could be used to estimate the expected needle position. For example, where only the immediately previous image is available, the region of interest could include the needle plus a relatively large distance along its trajectory beyond the needle tip. Where two previous images are available, the region of interest could include the needle plus a distance along its trajectory beyond the needle tip, wherein the distance is determined from movement of the needle registered from the two previous images.

While, in the described embodiment, an object of interest in the ultrasound images is a needle, those skilled in the art will appreciate that the invention can be used in conjunction with other objects, such as, for example, biopsy apparatus.

It can be advantageous in some cases to compare a US image to one or more previous US images. For example, where the target volume is expected to shift, the initial image of the target volume prior to insertion of the needle may provide an inaccurate baseline image. By using more recent previous images, the target volume can be, in some cases, more readily filtered out to generate a cleaner difference map.

While the US images are pre-filtered to identify voxels that are adjacent other voxels along the expected direction that the needle longitudinally extends, other methods of filtering the images will occur to those skilled in the art. Voxels corresponding to other characteristics of an object can be identified to filter out other voxels that do not correspond to the same.

The above-described embodiments are intended to be examples of the present invention and alterations and modifications may be effected thereto, by those of skill in the art, without departing from the scope of the invention which is defined solely by the claims appended hereto.

What is claimed is:

1. A method of registering a needle in a patient target volume in an ultrasound imaging system, comprising:
   capturing a first ultrasound image of the patient target volume using an ultrasound probe prior to insertion of the needle into said patient target volume;
   capturing a second ultrasound image of a sub-sector of said patient target volume using the ultrasound probe after insertion of the needle into said patient target volume, said sub-sector corresponding generally to a predicted trajectory of the needle within said patient target volume;
   computing the actual trajectory of said needle in said patient target volume using a computing device, based on differences detected between said first and second ultrasound images; and
   with the actual needle trajectory computed, computing a needle tip location and an entry location of the needle into said patient target volume, wherein said actual needle trajectory computing comprises:
   generating a difference map from said first and second examining said difference map from said first and second ultrasound images;
   examining said difference map from said first and second ultrasound images;
   fitting a line to the voxels representing the needle; and
   using the equation of the line to represent said actual needle trajectory.

2. The method of claim 1 wherein said difference map generating comprises:
   comparing each pair of corresponding voxels of said first and second ultrasound images to determine a resultant difference voxel for each pair;
   examining each difference voxel to determine if its magnitude exceeds a threshold; and
   populating the difference map with difference voxels having magnitudes exceeding the threshold.

3. The method of claim 2 further comprising filtering the difference map to remove voxels deemed to be noise.

4. The method of claim 3 wherein said filtering comprises:
   examining voxels of said difference map to detect voxels that are more than a threshold distance from the predicted needle trajectory; and
   removing the detected voxels from said difference map.

5. The method of claim 4 wherein said line is fitted to the voxels using linear regression analysis.

6. The method of claim 4 wherein said actual needle trajectory computing further comprises removing voxels in said difference map that are beyond a threshold distance from the predicted needle trajectory.

7. The method of claim 6 wherein said needle tip location computing comprises determining the voxel in said difference map that is positioned furthest along said actual needle trajectory.

8. The method of claim 7 wherein said needle entry location computing comprises calculating the intersection of the actual needle trajectory with a known needle patient target volume entry plane.

9. The method of claim 8 further comprising generating an ultrasound image of a plane within said patient target volume including said needle.

10. The method of claim 9 wherein said ultrasound image generating comprises:
    capturing a third ultrasound image of the patient target volume using the ultrasound probe;
    selecting an arbitrary point in said third ultrasound image;
    defining a plane coplanar with the needle using the needle tip location, the needle entry location and the arbitrary point; and
    extracting ultrasound image data along said plane to generate the ultrasound image of said plane.

11. The method of claim 10 wherein selecting the arbitrary point to be on a line intersecting the needle entry location and parallel to a y-axis, defines a sagital-oblique plane and wherein selecting the arbitrary point to be on a line intersecting the needle entry location and parallel to an x-axis defines a coronal oblique plane.

12. The method of claim 1 wherein said line is fitted to the voxels using linear regression analysis.

13. The method of claim 12 wherein said actual needle trajectory computing further comprises removing voxels in said difference map that are beyond a threshold distance from the predicted needle trajectory.

14. The method of claim 13 wherein said needle tip location computing comprises determining the voxel in said difference map that is positioned furthest along said actual needle trajectory.

15. The method of claim 14 wherein said needle entry location computing comprises calculating the intersection of the actual needle trajectory with a known needle patient target volume entry plane.

16. The method of claim 15 further comprising generating an ultrasound image of a plane within said patient target volume including said needle.

17. The method of claim 16 wherein said ultrasound image generating comprises:
- capturing a third ultrasound image of the patient target volume using the ultrasound probe;
- selecting an arbitrary point in said third ultrasound image;
- defining a plane coplanar with the needle using the needle tip location, the needle entry location and the arbitrary point; and
- extracting ultrasound image data along said plane to generate the ultrasound image of said plane.

18. The method of claim 17 wherein selecting the arbitrary point to be on a line intersecting the needle entry location and parallel to a y-axis, defines a sagital-oblique plane and wherein selecting the arbitrary point to be on a line intersecting the needle entry location and parallel to an x-axis defines a coronal oblique plane.

19. A method, comprising:
- imaging a patient target volume using an elongate ultrasound probe and generating a three-dimensional ultrasound image of said patient target volume;
- inserting a needle into said patient target volume using a needle driving apparatus;
- imaging a sub-sector of said patient target volume using said elongate ultrasound probe and generating a three-dimensional ultrasound image of said patient target volume sub-sector, said patient target volume sub-sector encompassing a predicted trajectory of the needle within said patient target volume;
- computing the actual trajectory of said needle in said patient target volume using a computing device based on differences detected between the patient target volume three-dimensional ultrasound image and the patient target volume sub-sector three-dimensional ultrasound image; and
- with the actual needle trajectory computed, computing a needle tip location and an entry location of the needle into said patient target volume, wherein said actual needle trajectory computing comprises:
  - generating a difference map from said patient target volume and patient target volume sub-sector ultrasound images;
  - examining said difference map to determine voxels representing the needle;
  - fitting a line to the voxels representing the needle; and
  - using the equation of the line to represent said actual needle trajectory.

20. The method of claim 19 further comprising:
- mapping a coordinate system of said elongate ultrasound probe to a coordinate system of said needle driving apparatus; and
- using needle position information from said needle driving apparatus to determine said predicted needle trajectory.

21. The method of claim 20 wherein said difference map generating comprises:
- comparing each pair of corresponding voxels of said patient target volume and patient target volume sub-sector ultrasound images to determine a resultant difference voxel for each pair;
- examining each difference voxel to determine if its magnitude exceeds a threshold; and
- populating the difference map with difference voxels having magnitudes exceeding the threshold.

22. The method of claim 21 further comprising filtering the difference map to remove voxels deemed to be noise.

23. The method of claim 22 wherein said filtering comprises:
- examining voxels of said difference map to detect voxels that are more than a threshold distance from the predicted needle trajectory; and
- removing the detected voxels from said difference map.

24. The method of claim 19 wherein said line is fitted to the voxels using linear regression analysis.

25. The method of claim 23 wherein said actual needle trajectory computing further comprises removing voxels in said difference map that are beyond a threshold distance from the predicted needle trajectory.

26. The method of claim 25 wherein said needle tip location computing comprises determining the voxel in said difference map that is positioned furthest along said actual needle trajectory.

27. The method of claim 26 wherein said needle entry location computing comprises calculating the intersection of the actual needle trajectory with a known needle patient target volume entry plane.

28. The method of claim 26 further comprising generating an ultrasound image of a plane within said patient target volume including said needle.

29. The method of claim 28 wherein said ultrasound image generating comprises:
- capturing a third ultrasound image of the patient target volume using said elongate ultrasound probe;
- selecting an arbitrary point in said third ultrasound image;
- defining a plane coplanar with the needle using the needle tip location, the needle entry location and the arbitrary point; and
- extracting ultrasound image data along said plane to generate an ultrasound image of said plane.

30. The method of claim 23 further comprising generating an ultrasound image of a plane within said patient target volume including said needle.

31. The method of claim 30 wherein said ultrasound image generating comprises:
- capturing a third ultrasound image of the patient target volume using said elongate ultrasound probe;
- selecting an arbitrary point in said third ultrasound image;
- defining a plane coplanar with the needle using the needle tip location, the needle entry location and the arbitrary point; and
- extracting ultrasound image data along said plane to generate an ultrasound image of said plane.

32. A system, comprising:
- an ultrasound transducer configured to image a patient target volume prior to insertion of a needle in said patient target volume and imaging a sub-sector of said patient target volume after insertion of the needle in said patient target volume, said patient target volume sub-sector encompassing a predicted trajectory of the needle within said patient target volume;
- a needle driving apparatus configured to insert a needle into said patient target volume; and
- a processor communicating with said ultrasound transducer and said needle driving apparatus, said processor configured to compute the actual trajectory of said needle in said patient target volume using differences detected between the imaged patient target volume and the imaged patient target volume sub-sector and with the actual needle trajectory computed, said processor configured to compute a needle tip location and an entry location of the needle into said patient target volume, wherein during said actual needle trajectory, computing said processor is configured to:
  generate a difference map from said imaged patient target volume and said imaged patient target volume sub-sector;
  examine said difference map to determine voxels representing the needle;
  fit a line to the voxels representing the needle; and
  use the equation of the line to represent said actual needle trajectory.

33. The system of claim 32 wherein said processor is configured to map a coordinate system of said ultrasound transducer to a coordinate system of said needle driving apparatus and to use needle position information from said needle driving apparatus to determine said predicted needle trajectory.

34. The system of claim 33 wherein during difference map generating, said processor is configured to compare each pair of corresponding voxels of said imaged patient target volume and said imaged patient target volume sub-sector to determine a resultant difference voxel for each pair, to examine each difference voxel to determine if its magnitude exceeds a threshold and to populate the difference map with difference voxels having magnitudes exceeding the threshold.

35. The system of claim 34 wherein said processor is configured to filter the difference map to remove voxels deemed to be noise.

36. The system of claim 35 wherein during needle tip location computing, said processor is configured to determine the voxel in said difference map that is positioned furthest along said actual needle trajectory.

37. The system of claim 36 wherein during needle entry location computing, said processor is configured to calculate the intersection of the actual needle trajectory with a known needle patient target volume entry plane.

38. The system of claim 33 wherein said processor is configured to generate an ultrasound image of a plane within said patient target volume including said needle.

39. The system of claim 38 wherein during ultrasound image generating, said processor is configured to capture a third ultrasound image of the patient target volume, is configured to select an arbitrary point in said third ultrasound image, is configured to define a plane coplanar with the needle using the needle tip location, the needle entry location and the arbitrary point and is configured to extract ultrasound image data along said plane to generate an ultrasound image of said plane.

* * * * *